(12) United States Patent
Canh et al.

(10) Patent No.: US 9,220,699 B2
(45) Date of Patent: Dec. 29, 2015

(54) COMPLEX CONTAINING CARBOXYL SUBSTITUTED STARCH AND LIPID FOR DELAYED DELIVERY OF ACTIVE INGREDIENTS

(71) Applicants: Le Tien Canh, Montreal (CA); Mihaela Friciu, Dorval (CA); Pompilia Ispas-Szabo, Longueuil (CA); Mircea Alexandru Mateescu, Montreal (CA)

(72) Inventors: Le Tien Canh, Montreal (CA); Mihaela Friciu, Dorval (CA); Pompilia Ispas-Szabo, Longueuil (CA); Mircea Alexandru Mateescu, Montreal (CA)

(73) Assignee: KARICI DIAGNOSTICS INC., Montreal (CA)

( * ) Notice: Subject to any disclaimer, the term of this patent is extended or adjusted under 35 U.S.C. 154(b) by 0 days.

(21) Appl. No.: 14/398,055

(22) PCT Filed: Apr. 30, 2013

(86) PCT No.: PCT/CA2013/000431
§ 371 (c)(1),
(2) Date: Oct. 30, 2014

(87) PCT Pub. No.: WO2013/163738
PCT Pub. Date: Nov. 7, 2013

(65) Prior Publication Data
US 2015/0110883 A1    Apr. 23, 2015

Related U.S. Application Data

(60) Provisional application No. 61/640,597, filed on Apr. 30, 2012.

(51) Int. Cl.
*A61K 9/20*    (2006.01)
*A61K 31/196*    (2006.01)
*A61K 9/28*    (2006.01)
*A61K 47/48*    (2006.01)

(52) U.S. Cl.
CPC .............. *A61K 31/196* (2013.01); *A61K 9/2866* (2013.01); *A61K 47/4823* (2013.01); *A61K 47/48046* (2013.01); *A61K 47/48053* (2013.01); *A61K 9/2013* (2013.01); *A61K 9/2059* (2013.01)

(58) Field of Classification Search
None
See application file for complete search history.

(56) References Cited

U.S. PATENT DOCUMENTS

2004/0127476 A1* 7/2004 Kershman et al. ............ 514/177
2008/0044481 A1   2/2008 Harel

FOREIGN PATENT DOCUMENTS

CA    2765033         12/2010
CA    2765033 A1 *    12/2010
(Continued)

OTHER PUBLICATIONS

Fricium, M.Met al. "Carboxymethyl starch and lecithin complex as matric for targeted drug delivery; I. Monolithic Mesalamine forms for colon delevery" European Journal ofPharmaceutics and Biopharmaceutics. 2013. In press—Published online—Apr. 3, 2013.
(Continued)

*Primary Examiner* — Robert A Wax
*Assistant Examiner* — Melissa Mercier
(74) *Attorney, Agent, or Firm* — Benoît & Côté Inc.

(57) ABSTRACT

The present document describes a composition for sustained, targeted or sustained and targeted delivery of an active ingredient which includes a complex formed between a carboxyl substituted polymer and a lipid. The present document also describes dosage forms containing the composition, and an active ingredient, and methods of using the same for the treatment of diseases.

17 Claims, 12 Drawing Sheets

(56) References Cited

FOREIGN PATENT DOCUMENTS

| CN | 1524582 A | * | 9/2004 |
|---|---|---|---|
| CN | 102488198 | | 6/2012 |
| CN | 1524582 | | 8/2013 |
| GB | 837451 | | 6/1960 |
| GB | 862376 | | 3/1961 |

OTHER PUBLICATIONS

PCT—International Search Report (ISR)—PCT/CA2013/000431 (Form PCT/ISA/220)—Aug. 13, 2013—5 pages.

Nabais et al. "High-amylose carboxymethyl starch matrices for oral sustained drug-release: In vitro and in vivo evaluation", European Journal of Pharmaceutics and Biopharmaceutics, vol. 65, No. 3, Feb. 28, 2007, pp. 371-378.

Assaad et al. "The influence of protonation ratio on properties of carboxymethyl starch excipient at various substitution degrees: Structural insights and drug release kinetics", International Journal of Pharmaceutics, Jul. 15, 2010, vol. 394, No. 1-2, pp. 75-84.

Supplementary European Search Report of No. EP13784599.6, Munich, May 8, 2015, Antonio Raposo.

* cited by examiner

COMPLEX CONTAINING CARBOXYL SUBSTITUTED STARCH AND LIPID FOR DELAYED DELIVERY OF ACTIVE INGREDIENTS

CROSS-REFERENCE TO RELATED APPLICATIONS

This application is a national phase of International Application under 35 USC §371 of PCT/CA2013/000431, filed Apr. 30, 2013, which claims priority and the benefit under 35 USC §119(e) of U.S. provisional patent application 61/640,597, filed on Apr. 30, 2012, the specifications of which are hereby incorporated by reference, in their entireties.

BACKGROUND (a) Field

The subject matter disclosed generally relates to complex structure containing carboxyl substituted starch and lipid for delayed delivery of drugs, including medications used to treat the symptoms of Crohn's disease.

(b) Related Prior Art

Crohn's disease, also known as regional enteritis, is a type of inflammatory bowel disease that may affect any part of the gastrointestinal tract, causing a wide variety of symptoms. It primarily causes abdominal pain, diarrhea (which may be bloody if inflammation is at its worst), vomiting (can be continuous), or weight loss, but may also cause complications outside the gastrointestinal tract such as skin rashes, arthritis, inflammation of the eye, tiredness, and lack of concentration. Crohn's disease is caused by interactions between environmental, immunological and bacterial factors in genetically susceptible individuals. This results in a chronic inflammatory disorder, in which the body's immune system attacks the gastrointestinal tract possibly directed at microbial antigens. Crohn's disease has traditionally been described as an autoimmune disease, but recent investigators have described it as a disease of immune deficiency.

There is no known pharmaceutical or surgical cure for Crohn's disease. Treatment options are restricted to controlling symptoms, maintaining remission, and preventing relapse. Acute treatment uses medications to treat any infection (normally antibiotics) and to reduce inflammation (normally aminosalicylate anti-inflammatory drugs and corticosteroids). When symptoms are in remission, treatment enters maintenance, with a goal of avoiding the recurrence of symptoms. Prolonged use of corticosteroids has significant side-effects; as a result, they are, in general, not used for long-term treatment. Alternatives include aminosalicylates alone, though only a minority are able to maintain the treatment, and many require immunosuppressive drugs. On the other hand, it has been also suggested that antibiotics change the enteric flora, and their continuous use may pose the risk of overgrowth with pathogens such as *Clostridium difficile*.

Medications currently used to treat the symptoms of Crohn's disease include 5-aminosalicylic acid (5-ASA) formulations (Mesalamine), prednisone, immunomodulators such as azathioprine, mercaptopurine, methotrexate, infliximab, adalimumab, certolizumab and natalizumab. Hydrocortisone should be used in severe attacks of Crohn's disease.

Medications to treat the symptoms of Crohn's disease have to be in a dosage form with a timed delivery (chrono-delivery) to occur in the colon area of the GI tract. There are numerous problems with this chrono-delivery of the medications, i) pH in the colon area is around 7 and ii) the dosage form must be coated to prevent dissolution in the stomach.

It is highly desirable to have a dosage form for delivery of a medication in the colon, wherein the dosage form is simple to produce, is pH independent and has a high drug load.

SUMMARY

According to an embodiment, there is provided a composition for sustained, targeted or sustained and targeted delivery of an active ingredient comprising:
  a complex formed between a carboxyl substituted polymer and a lipid.

The complex may be in a ratio of the carboxyl substituted polymer and the lipid of about 10:1.

The carboxyl substituted polymer may be chosen from a carboxyl substituted starch, a carboxyl substituted cellulose, a carboxyl substituted polyvinyl alcohol, a pectin, an alginate, or combinations thereof.

The carboxyl substituted starch comprises carboxymethyl starch.

The carboxyl substituted starch may be carboxymethyl starch.

The carboxyl substituted cellulose may be carboxymethyl cellulose.

The carboxyl substituted polymer may be crosslinked or uncrosslinked.

The lipid may be at least one of a fatty acid, a glyceride, a lecithin, a phospholipid, an esterquat, or combinations thereof.

The glyceride may be at least one of a monoglyceride, a diglyceride a triglyceride or combinations thereof.

The phospholipid may be at least one of phosphatidylcholine, phosphatidylethanolamine, phosphatidylinositol, or combinations thereof.

The lecithin comprises phosphoric acid, choline, a fatty acid, glycerol, a glycolipid, a triglyceride, and a phospholipid.

According to another embodiment, there is provided a dosage form for sustained, targeted or sustained and targeted of an active ingredient comprising:
  a composition of the present invention, and
  an active ingredient.

The active ingredient may be mesalamine.

The dosage form may further comprise a coating.

The coating may be a polysaccharide polymer.

The polysaccharide polymer may be ethyl cellulose.

The ratio of the active ingredient and the complex may be from about 77:23 to about 73:27.

The ratio of the active ingredient and the complex may be about 76:24.

The dosage form may be chosen from a capsule, a powder, a tablet, a bead and a microsphere.

According to another embodiment, there is provided a method of delivering an active ingredient to a gastro-intestinal compartment comprising administering to a person in need thereof a dosage form as described above.

The gastro-intestinal compartment may be the colon.

According to another embodiment, there is provided a method for the preparation of a dosage form as described above comprising:
  a) admixing the active ingredient with the complex comprising a carboxyl substituted polymer and a lipid.

According to another embodiment, there is provided a use of the dosage form as described above for delivery of an active ingredient to a gastro-intestinal compartment.

The gastro-intestinal compartment may be the colon.

The dosage form may be for the treatment of Crohn's disease.

The following terms are defined below.

The term "chrono-delivery" is intended to mean the delivery of an active ingredient after a predetermined period of time, in order to target the release in specific regions of the gastro intestinal tract.

The term "esterquat" is intended to mean a class of surface active quaternary ammonium compounds having general formula $RN^+X^-$ where R is generally a fatty acid moiety, and $X^-$ a suitable anion.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

DETAILED DESCRIPTION

The present invention is based on the inclusion of lipids which is carried out with modified starch, particularly with carboxymethyl starch. The lipids included with modified starch can monoalkyl chains (i.e. monoglyceride), but also di- or tri-alkyl chains (i.e. phospholipids and triglyceride, respectively).

In embodiments there is disclosed a composition for chrono-delivery of an active ingredient which comprises a complex comprising a carboxyl substituted polymer and a lipid. The composition allows the sustained, targeted or sustained and targeted delivery of an active ingredient. According to an embodiment, the carboxyl substituted polymer may be chosen from a carboxyl substituted starch, a carboxyl substituted cellulose, a carboxyl substituted polyvinyl alcohol, a pectin, an alginate, or combinations thereof. Preferably, the carboxyl substituted starch comprises carboxymethyl starch, with other carboxyl substituted polymers, or alone. According to another embodiment, the carboxyl substituted cellulose is carboxymethyl cellulose.

According to some embodiments, the carboxyl substituted polymer is crosslinked or uncrosslinked.

According to an embodiment, the lipid is at least one of a fatty acid, a glyceride (e.g. omega-3 oil), a lecithin, a phospholipid, an esterquat, or combinations thereof. The glyceride may be at least one of monoglyceride, diglyceride or triglyceride or combinations thereof. The phospholipid may be at least one of phosphatidylcholine, phosphatidylethanolamine, phosphatidylinositol, or combinations thereof. The lecithin may comprise phosphoric acid, choline, a fatty acid, glycerol, a glycolipid, a triglyceride, and a phospholipid.

Figure 1:
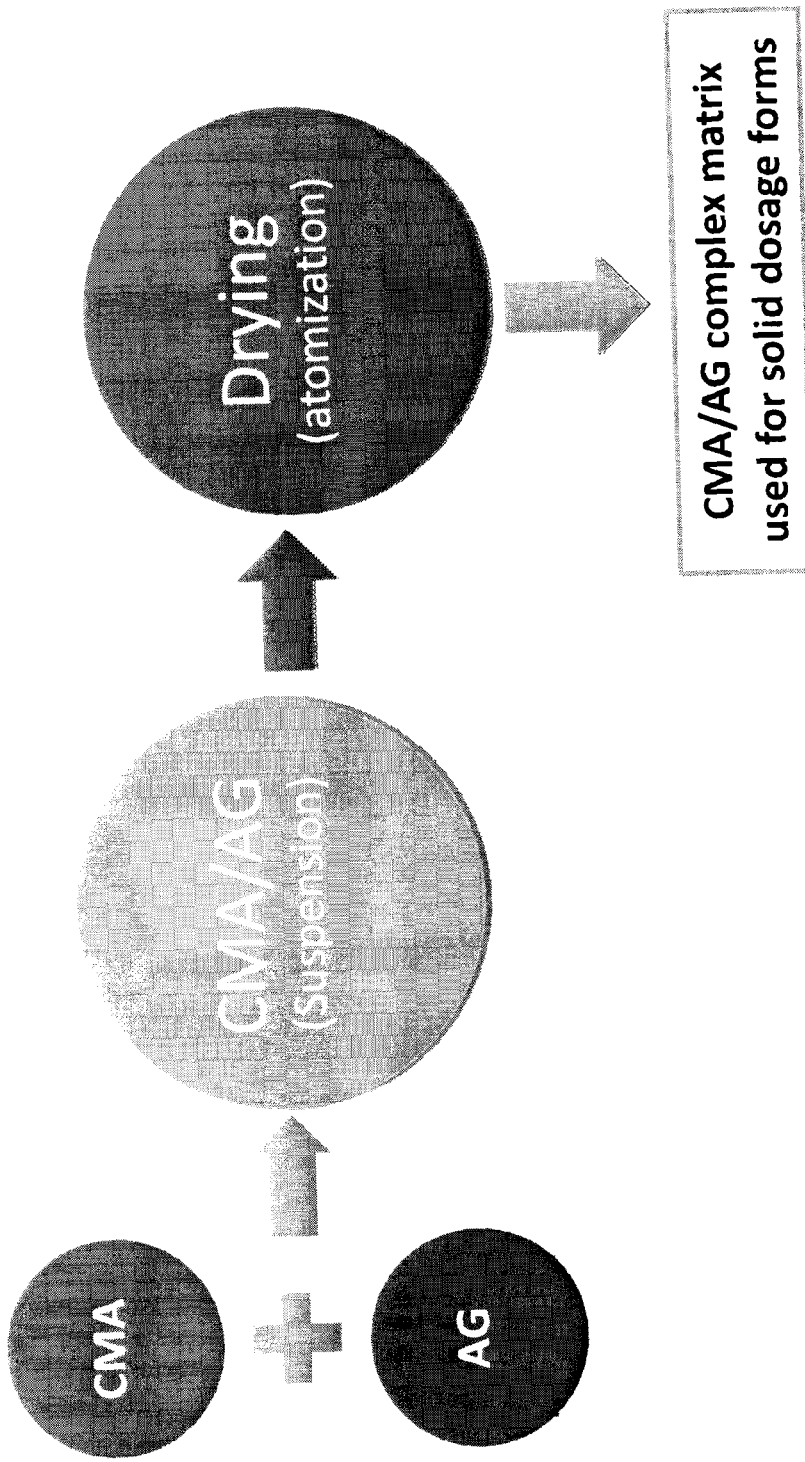
FIG. 1 illustrates the preparation of a complex comprising a carboxyl substituted polymer and a lipid according to an embodiment of the present invention. CMA: Carboxymethyl Starch; AG: Lipid.

According to an embodiment of the present invention, the complex may be in a ratio of carboxyl substituted polymer and lipid of about 10:1. Now referring to FIG. 1, which shows solutions of carboxyl substituted polymer (e.g. CMA) and lipid (AG), which are mixed to obtain a carboxyl substituted polymer and lipid suspension, which is dried (atomized) to obtain a solid matrix powder which may be used for direct formulation of dosage forms.

According to another embodiment, there is disclosed a dosage form for timed (chrono) delivery of an active ingredient which includes a composition of the present invention and an active ingredient. The dosage form may be any suitable dosage form, for example a capsule, a powder, a tablet, a bead and a microsphere. Active ingredient may be any desired and/or suitable drug for which delayed or controlled release over time, at a desired location, is desired. For example, the active ingredient may be antibiotics such as metronidazole, immunosuppressive drugs such as azathiopurine, NSAIDs such as diclofenac, and mesalamine. According to another embodiment, the active ingredient may also include natural products, such as for example natural molecules and enzymes.

According to another embodiment, the dosage form may further comprise a coating. The coating may be, for instance, a polysaccharide polymer coating, for example an ethyl cellulose polymer.

According to another embodiment, the dosage form may have a ratio of the active ingredient and the complex from about 77:23 to about 73:27. Preferably, the ratio of the active ingredient and the complex is about 76:24. The dosage form of the present invention may be prepared according to a method which involves admixing the active ingredient with the complex comprising a carboxyl substituted polymer and a lipid of the present invention.

According to another embodiment, there is disclosed a method of delivering an active ingredient to a gastro-intestinal compartment by administering to a person in need thereof a dosage form according to the present invention. According to another embodiment, there is also disclosed the use of the dosage form of the present invention for delivery of an active ingredient to a gastro-intestinal compartment. Preferably, the gastro-intestinal compartment is the colon. For example, the dosage form of the present invention may be used for the treatment of Crohn's disease.

The present invention will be more readily understood by referring to the following examples which are given to illustrate the invention rather than to limit its scope.

Example 1

Mesalamine Formulation

A mesalamine formulation is prepared according to table 1:

TABLE 1

| Ingredients | Percentage (%) |
|---|---|
| Mesalamine (M) | 74 (400 mg) |
| Complexe CMA/AG | 26 (140 mg) |
| Total | 100 (540 mg) |

The formulation is easily prepared by direct compression of the powders of complex CMA/AG and mesalamine.

Example 2

Study of Mesalamine Formulation

Figure 2:
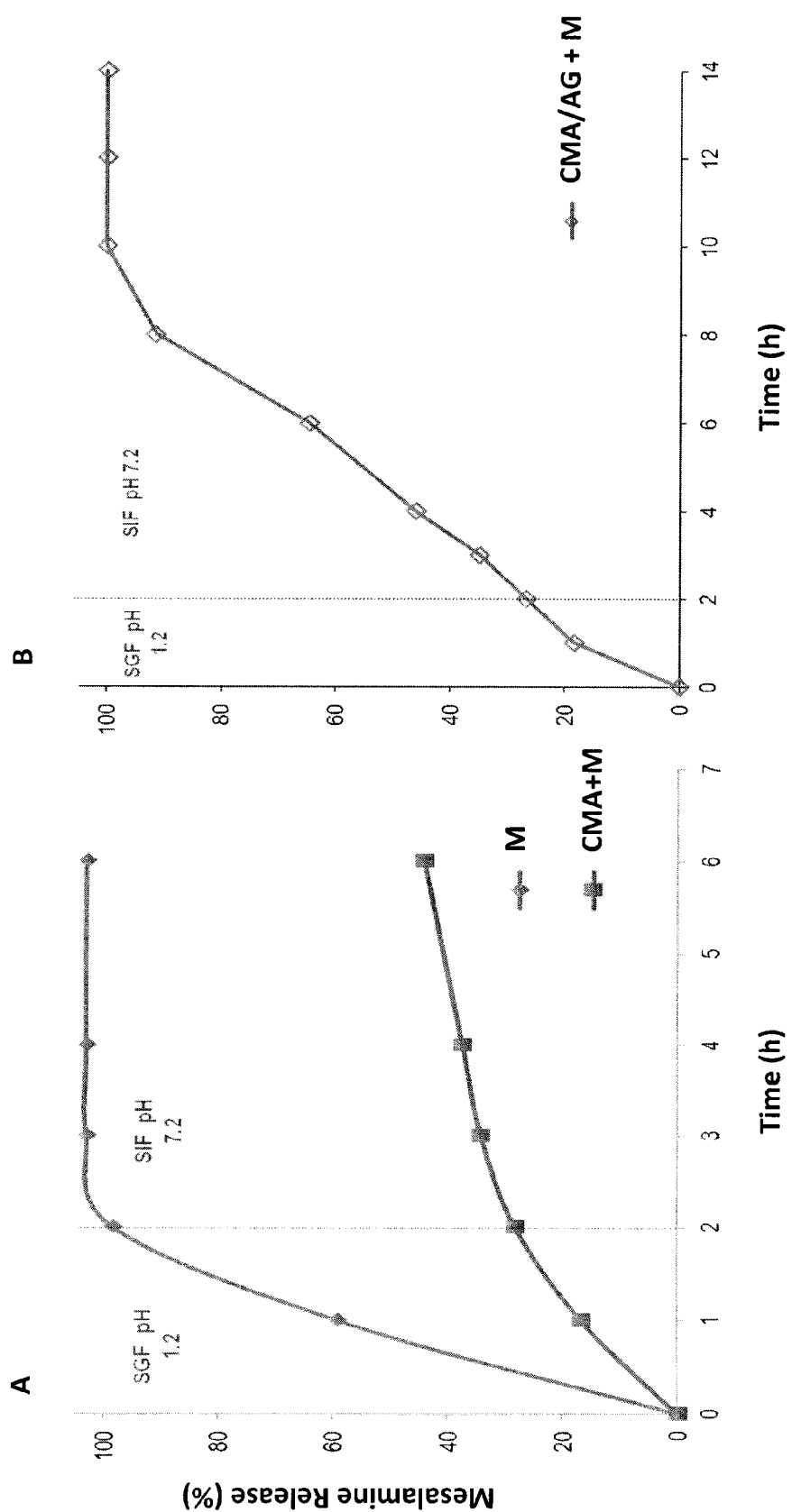
FIG. 2 illustrates (A) the release of mesalamine alone or in a formulation comprising carboxymethyl starch, (B) that the addition of a lipid (AG) eliminates the interaction with mesalamine, but results in partial gastric release, and (C) that the addition of a coating limits the release in the stomach and in the duodenum. In this case, the release occurs in a targeted manner in the colon. SGF: Simulated Gastric Fluid; SIF: Simulated Intestinal Fluid; CMA: Carboxymethyl Starch; AG: Lipid; M: Mesalamine (active ingredient).
Figure 2:
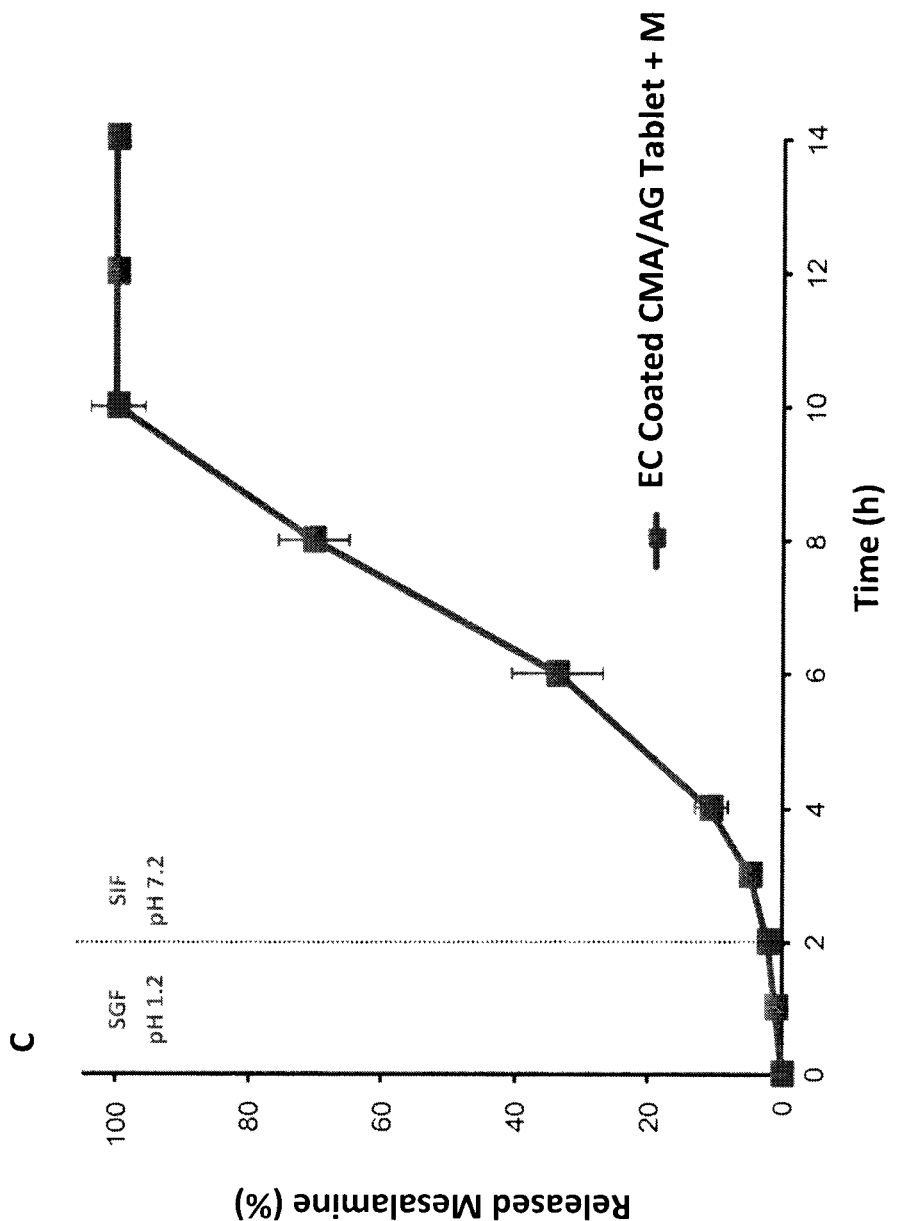

Now referring to FIG. 2, tablets as prepared in Example 1 are incubated in simulated gastric fluid (SGF)—(2 h)—pH 1.2 without pepsin and then in simulated intestinal fluid (SIF)—(8-14 h), pH 7.2 without pancreatine. FIG. 2A shows that interaction of the drug with carboxymethyl cellulose generates an incomplete release of the drug. Complexation with a lipid (lecithin), results in elimination of the interaction and complete release of the drug, but with a gastric release moderately higher (FIG. 2B). Coating of the tablets with a suitable material, such as ethylcellulose, which may be added by immersion or spraying of the table with a 15% solution of ethylcellulose in ethanol, eliminates the gastric and duodenal release while resulting in colonic release (FIG. 2C).

Example 3

Mesalamine Formulation and its Dissolution at Varying pH

Figure 3:
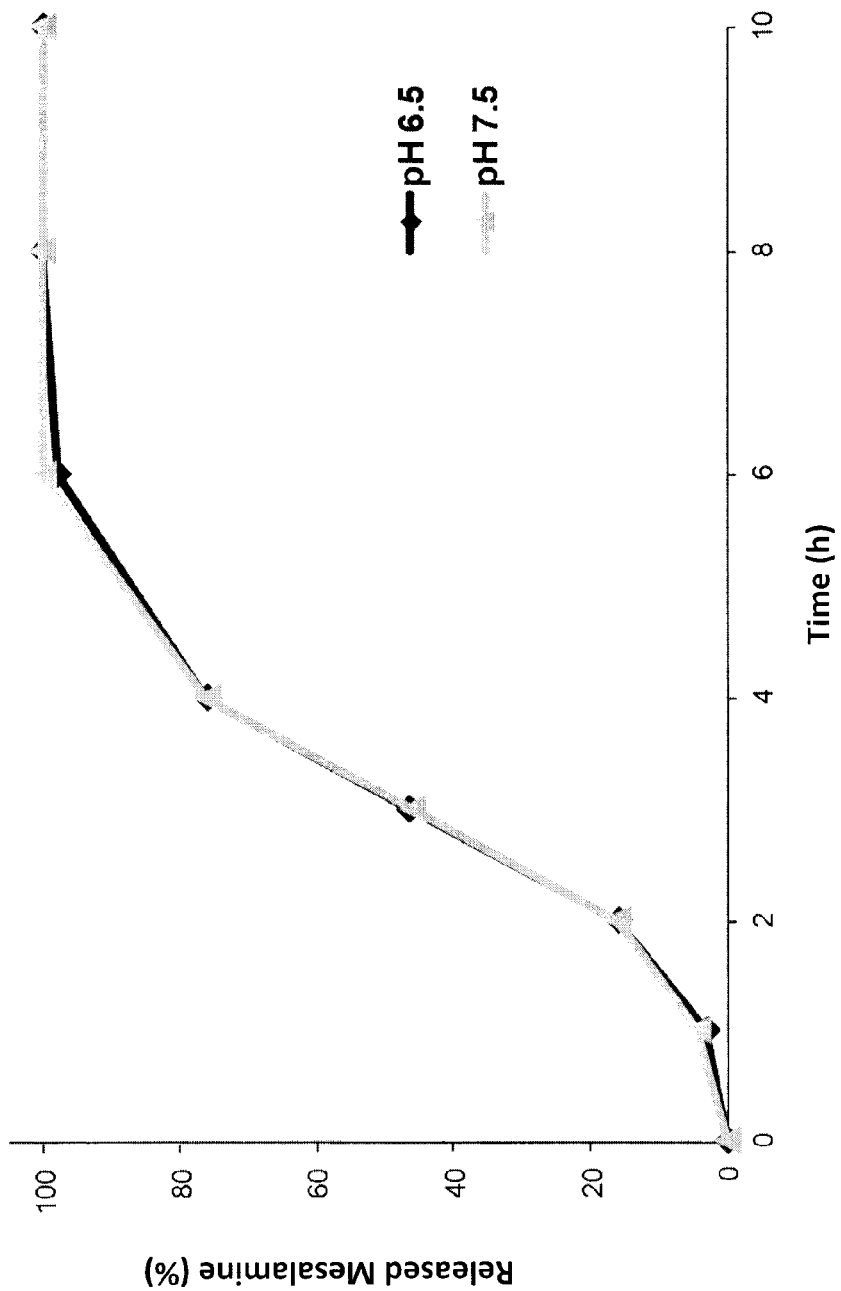
FIG. 3 illustrates that a complex comprising a carboxyl substituted polymer and a lipid according to an embodiment of the present invention allows release of mesalamine in a pH independent manner.

Now referring to FIG. 3 which illustrates dissolution of the tablets containing mesalamine in solutions at pH 6.5 vs. 7.5 and shows that the dissolution of the formulation of the present invention is pH independent.

Example 4

Modulation of the Amount of Complex in the Formulation

Figure 4:
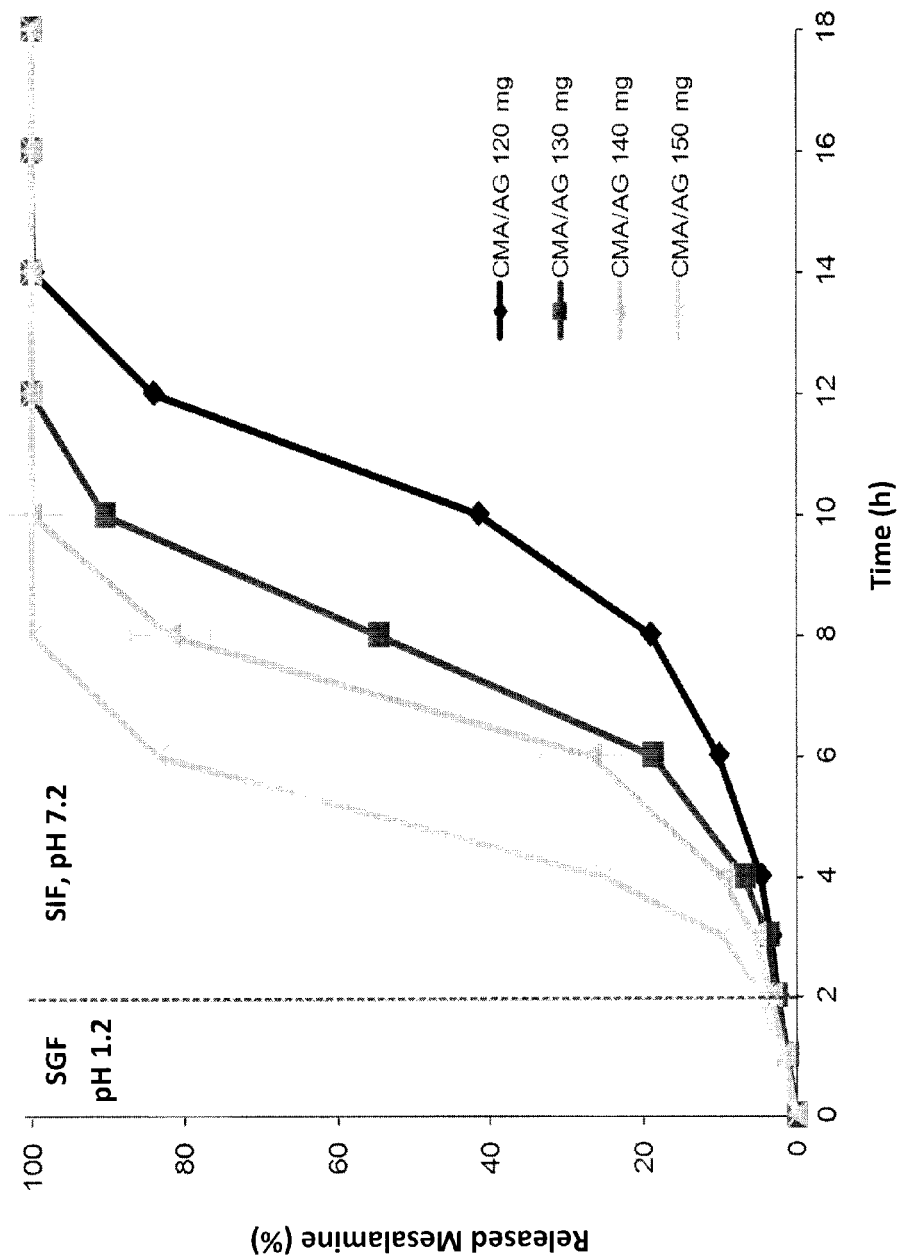
FIG. 4 illustrates that varying the ratio of complex comprising a carboxyl substituted polymer and a lipid and active ingredient (i.e. mesalamine), according to an embodiment of the present invention allows the modulation of the release of mesalamine over time. SGF: Simulated Gastric Fluid; SIF: Simulated Intestinal Fluid; CMA: Carboxymethyl Starch; AG: Lipid.

Now referring to FIG. 4, which shows that varying the amount of complex from about 23% (120 mg) to about 27% (150 mg) in the formulation allows to control the release of mesalamine over time, and to target the drug to the appropriate gastro-intestinal compartment.

Example 5

Structure of the Complex

Figure 5:
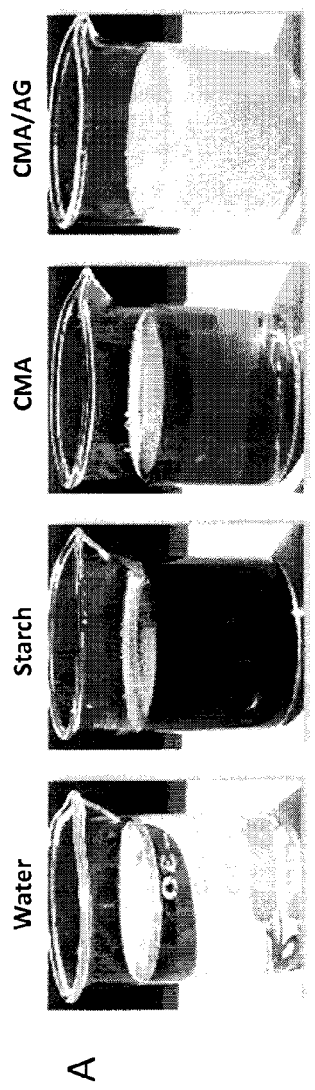
FIG. 5 illustrates (A) that the lipid (AG) prevents the inclusion of the iodine to form iodine/Carboxymethyl starch (CMA) complex, and (B) that the lipid (AG) is located inside the CMA helix.
Figure 5:
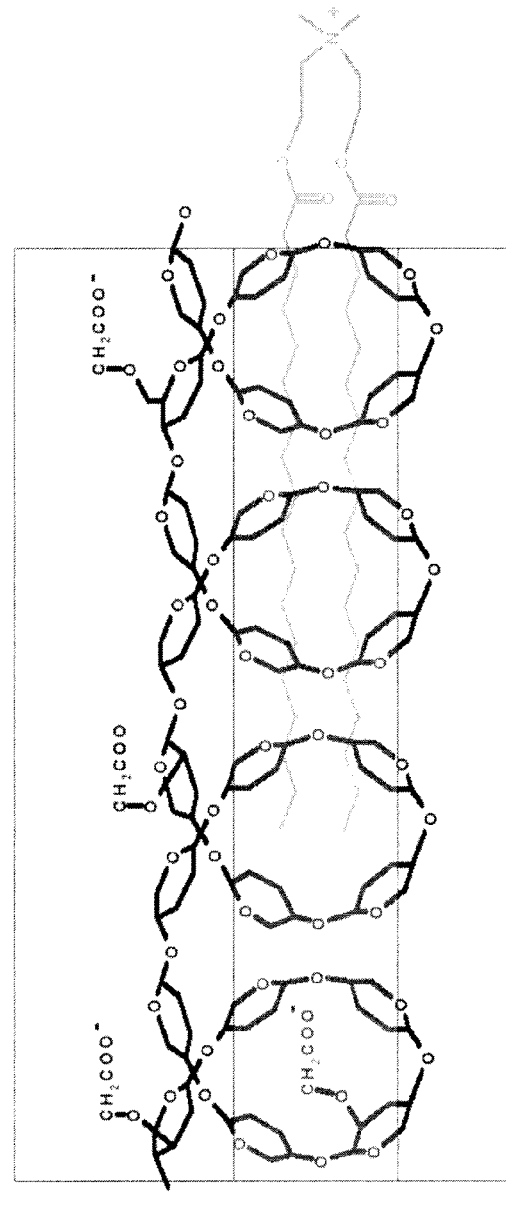

Now referring to FIG. 5A, which shows that incubation of iodine in the presence of carboxymethyl starch and lipid (CMA/AG) prevents the formation of carboxymethyl starch-iodine inclusion complexes suggesting that the lipid (AG) is located within the helix of the carboxymethyl starch polymer (See FIG. 5B).

Figure 6:
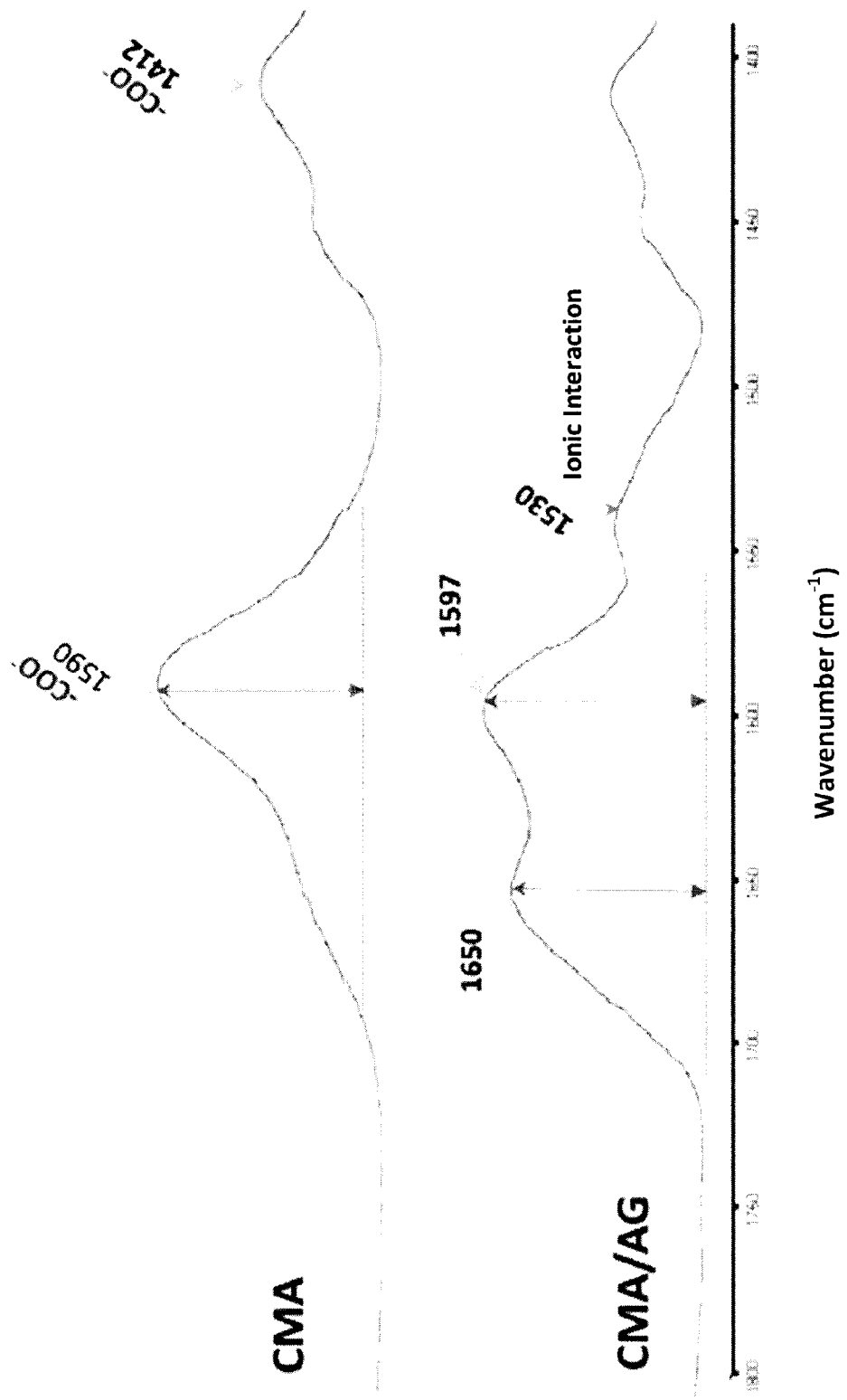
FIG. 6 illustrates FTIR spectra of tablets of Carboxymethyl starch (CMA) and of Carboxymethyl starch and lipid complex (CMA/AG) according to an embodiment of the present invention. CMA: Carboxymethyl Starch; AG: Lipid.
Figure 7:
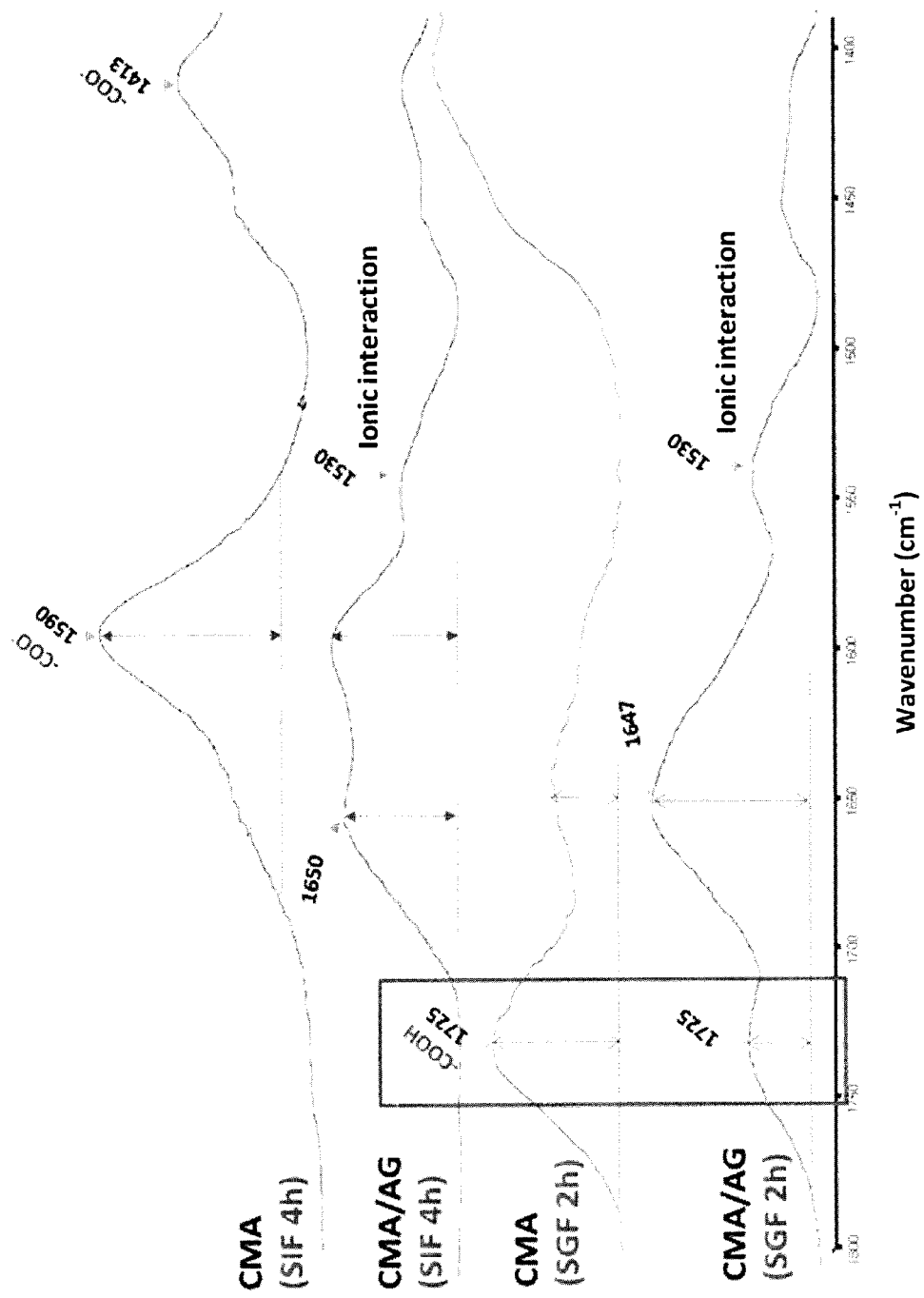
FIG. 7 illustrates FTIR spectra of tablets of Carboxymethyl starch (CMA) and of Carboxymethyl starch and lipid complex (CMA/AG) according to an embodiment of the present invention, following 2 h in simulated gastric fluid (SGF) or 4 h in simulated intestinal fluid (SIF).
Figure 8:
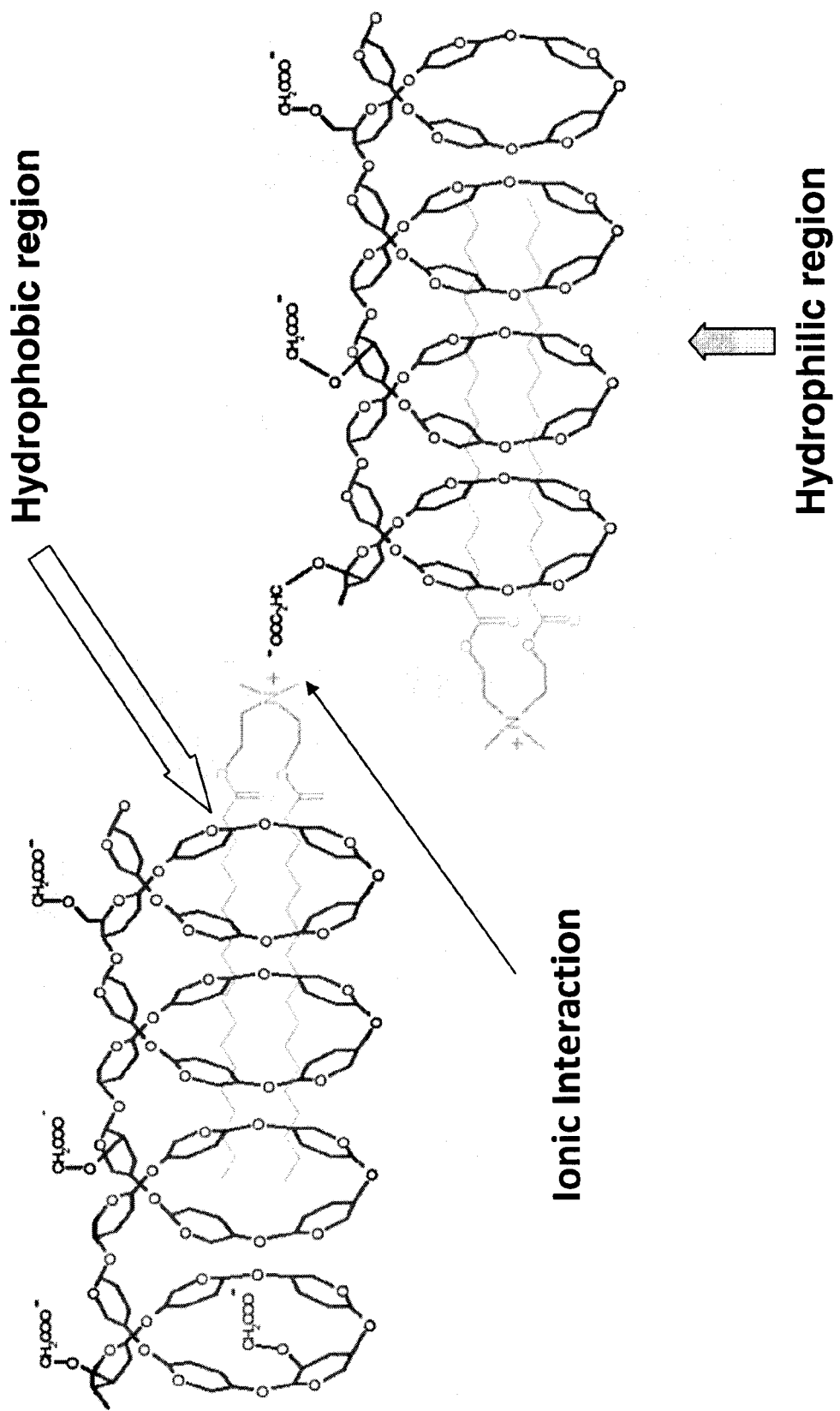
FIG. 8 illustrates the predicted ionic interaction within a Carboxymethyl starch and lipid complex (CMA/AG) according to an embodiment of the present invention. The FTIR spectra showed ionic interaction between the carboxylate groups and the amines of the fatty acids. SGF: Simulated Gastric Fluid; SIF: Simulated Intestinal Fluid; CMA: Carboxymethyl Starch; AG: Lipid.

In FIGS. 6-8, there is shown the FTIR spectra of CMA and of CMA/AG before incubation (FIG. 6) and after incubation in SIF for 4 h or 2 h in SGF (FIG. 7). The shift in the spectra is indicative of interactions between the ionic groups of the carboxymethyl starch and lipid. As summarized in FIG. 8, the FTIR spectra indicate molecular interactions between the carboxyl groups of the CMA and the amine of the lipid.

Figure 9:
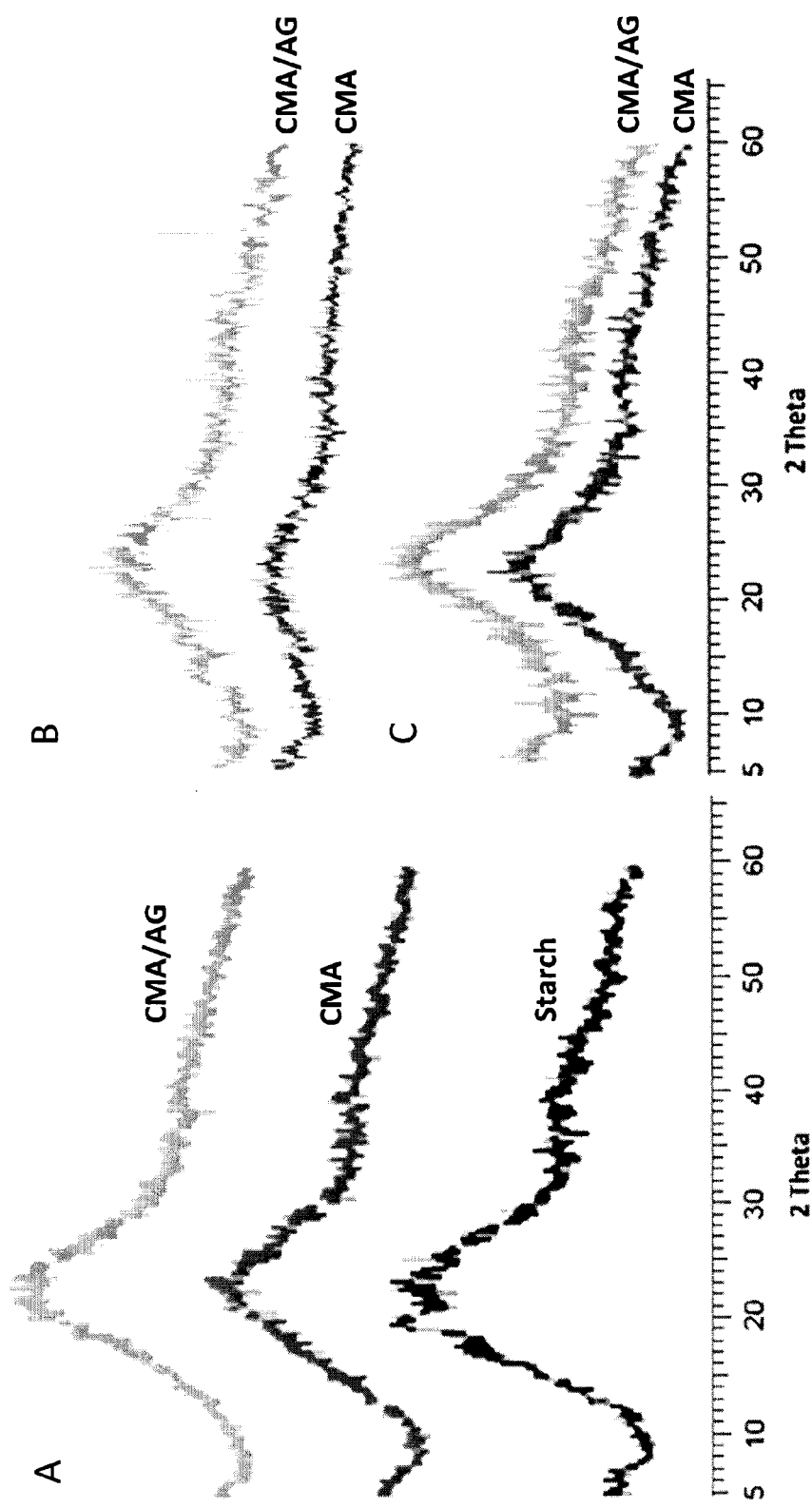
FIG. 9 illustrates the X-ray diffraction spectra of Carboxymethyl starch (CMA) and Carboxymethyl starch and lipid complex (CMA/AG) according to an embodiment of the present invention, untreated (A) and treated for 2 h in SGF (B) and 4 h in SIF (C).

FIG. 9 shows the X-ray diffraction spectra of FTIR spectra of CMA and CMA/AG before incubation and after incubation 2 h in SGF and 4 h in SIF. The SIF reduces the crystallinity of CMA, but not that of CMA/AG. The lipid therefore stabilizes the structure of the carboxyl polymer (CMA).

Figure 10:
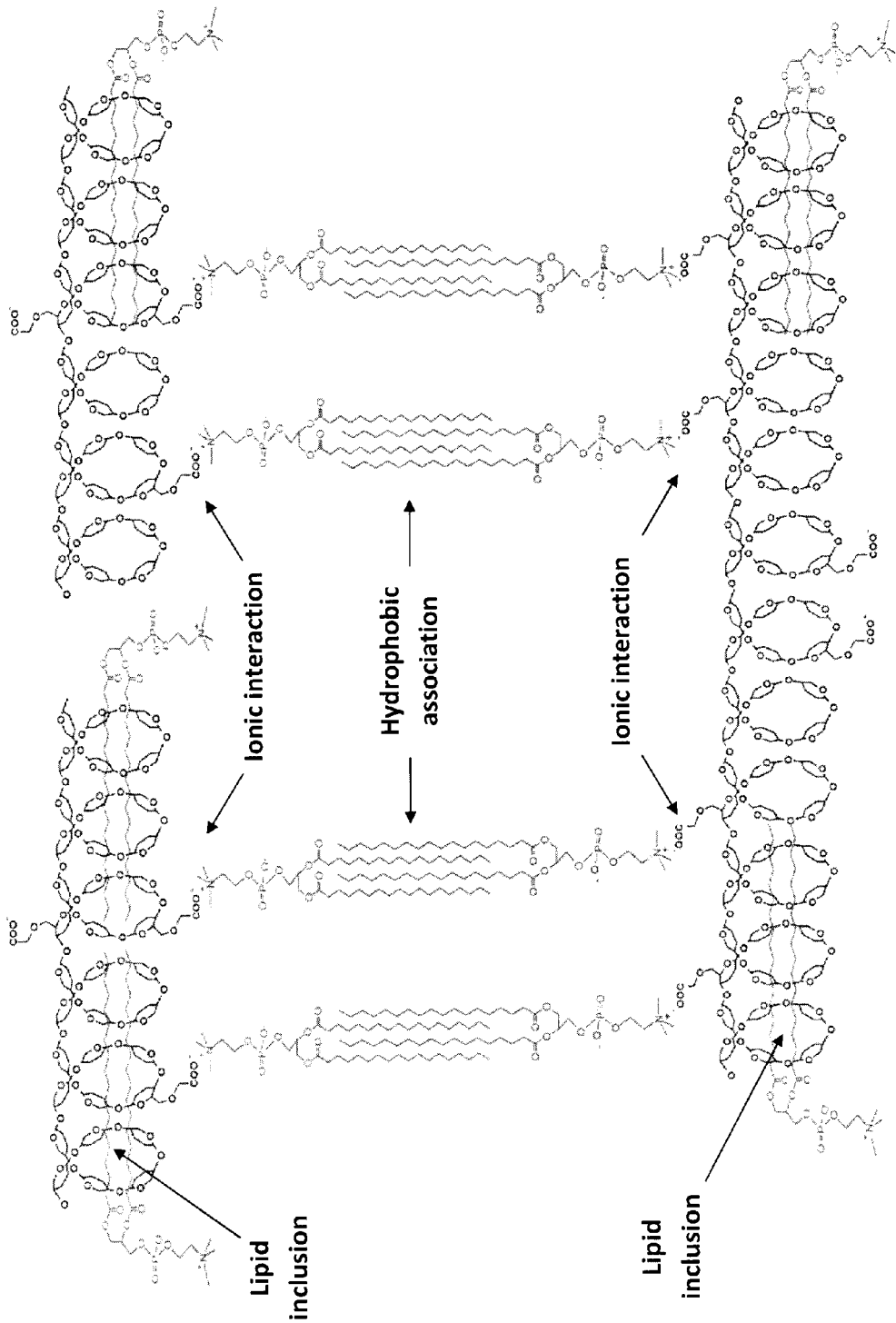
FIG. 10 illustrates a hypothetical structure of the Carboxymethyl starch and lipid complex (CMA/AG) according to an embodiment of the present invention.
Figure 11:
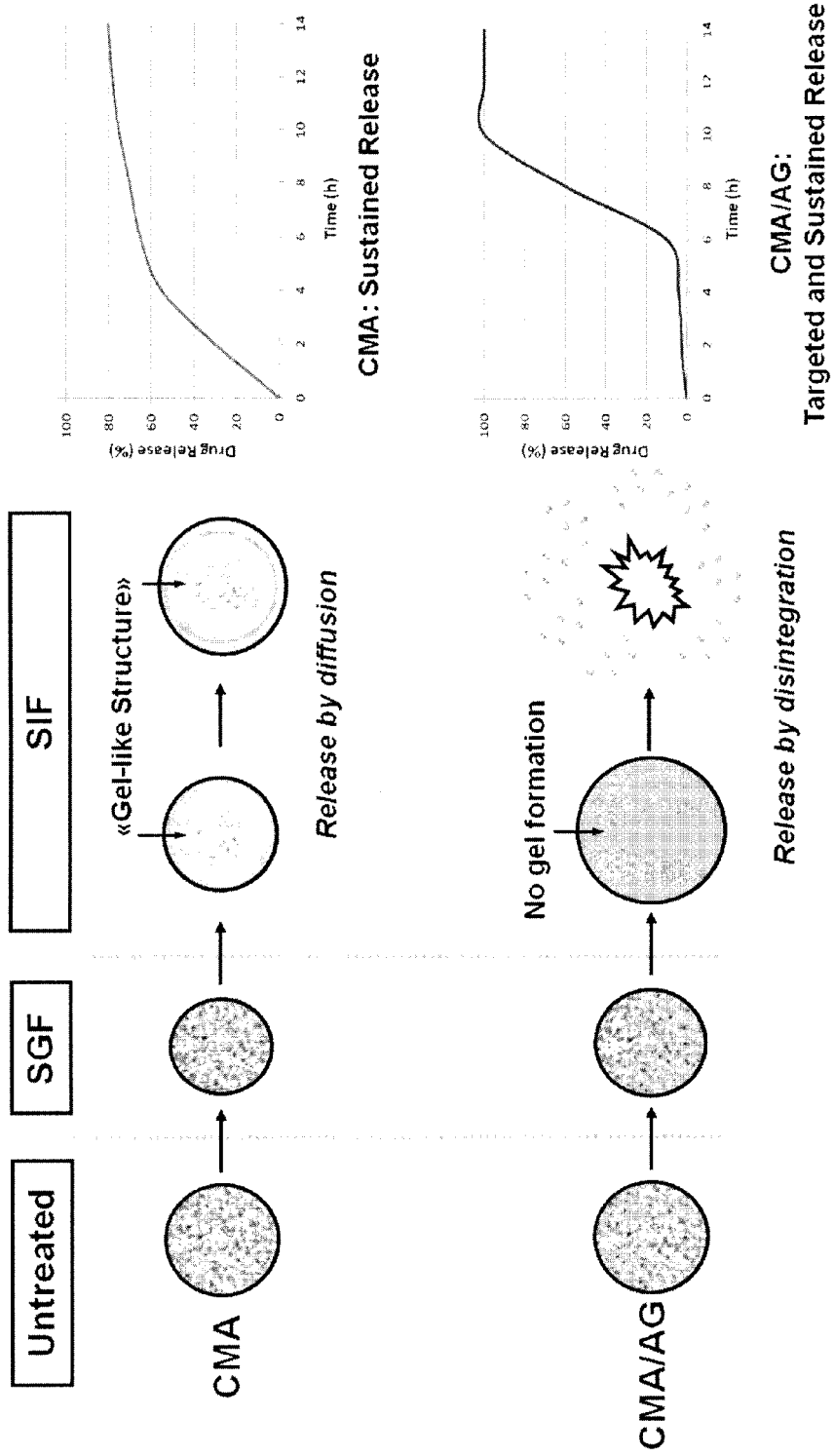
FIG. 11 illustrates a proposed mechanism of active ingredient release from Carboxymethyl starch (CMA) and from Carboxymethyl starch and lipid complex (CMA/AG) according to an embodiment of the present invention. SGF: Simulated Gastric Fluid; SIF: Simulated Intestinal Fluid; CMA: Carboxymethyl Starch; AG: Lipid.

FIG. 10 is a diagram of the hypothetical interactions between the carboxyl substituted polymer and the lipid, suggested by the experiments described above. As presented in FIG. 11, the carboxyl substituted polymer CMA alone is believed to release the active ingredient by diffusion, while the carboxyl substituted polymer and a lipid complex is believed to release the active ingredient by bursting of the structure of the complex, which causes a targeted and sustained release of the active ingredient. The carboxyl substituted polymer and the lipid are believed to form a complex at least by inclusion or other interactions such as hydrophobic interactions or ionic interaction.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:
1. A composition for sustained, targeted or sustained and targeted delivery of an active ingredient consisting of:
   a complex formed between an uncrosslinked carboxyl substituted polymer and a lipid consisting of a lecithin, a phospholipid, and an esterquat, or combinations thereof.

2. The composition of to claim 1, wherein said complex is in a ratio of said carboxyl substituted polymer and said lipid of about 10:1.

3. The composition of claim 1, wherein said carboxyl substituted polymer is chosen from a carboxyl substituted starch, a carboxyl substituted cellulose, a carboxyl substituted polyvinyl alcohol, a pectin, an alginate, or combinations thereof.

4. The composition of claim 3, wherein said carboxyl substituted starch is carboxymethyl starch.

5. The composition of claim 1, wherein said phospholipid is at least one of phosphatidylcholine, phosphatidylethanolamine, phosphatidylinositol, or combinations thereof.

6. A dosage form for sustained, targeted or sustained and targeted delivery of an active ingredient comprising:
   a composition as claimed in claim 1, and
   an active ingredient.

7. The dosage form of claim 6, wherein said active ingredient is mesalamine.

8. The dosage form of claim 6, further comprising a coating.

9. The dosage form of claim 8, wherein said coating is a polysaccharide polymer.

10. The dosage form of claim 9, wherein said polysaccharide polymer is ethyl cellulose.

11. The dosage form of claim 6, wherein a ratio of said active ingredient and said complex is from about 77:23 to about 73:27.

12. The dosage form of claim 6, wherein a ratio of said active ingredient and said complex is about 76:24.

13. The dosage form of claim 6, wherein said dosage form is chosen from a capsule, a powder, a tablet, a bead and a microsphere.

14. A method of delivering an active ingredient to a gastro-intestinal compartment comprising administering to a person in need thereof a dosage form as claimed in claim 6.

15. The method as claimed in claim 14, wherein said gastro-intestinal compartment is the colon.

16. A method for the preparation of a dosage form as claimed in claim 6 comprising:
   a) admixing said active ingredient with said complex formed between an uncrosslinked carboxyl substituted polymer and a lipid consisting of a lecithin, a phospholipid, and an esterquat, or combinations thereof.

17. The method of claim 14, wherein the dosage form is for the treatment of Crohn's disease.

* * * * *